US00PP09422P

United States Patent [19]

Zary

[11] Patent Number: Plant 9,422

[45] Date of Patent: Jan. 9, 1996

[54] HYBRID TEA ROSE PLANT NAMED 'JACMEM'

[75] Inventor: Keith W. Zary, Thousand Oaks, Calif.

[73] Assignee: Bear Creek Gardens, Inc., Medford, Oreg.

[21] Appl. No.: 382,866

[22] Filed: Feb. 9, 1995

[51] Int. Cl.[6] ..... A01H 5/00

[52] U.S. Cl. ..... Plt./15

[58] Field of Search ..... Plt./11, 15, 16

*Primary Examiner*—Howard J. Locker

*Attorney, Agent, or Firm*—Klarquist Sparkman Campbell Leigh & Whinston

[57] ABSTRACT

A rose plant of the hybrid tea class, characterized by the unique combination of its novel flower color; its dark green, glossy, powdery mildew resistant foliage; its long, strong stems; its excellent petal substance, and its heavily appendaged sepals.

1 Drawing Sheet

The present invention relates to a new and distinct variety of rose plant of the hybrid tea class which was originated by me by crossing the variety MERko, U.S. Plant Pat. No. 3,724, with the variety JACblem, U.S. Plant Pat. No. 4,847.

The primary objective of this breeding was to produce a new rose variety having the excellent petal substance, long vase life, and good cut-flower production of MERko combined with the longer stems, dark, glossy foliage, and powdery mildew resistance of JACblem. It was hoped flower color would fall between orange and yellow, the colors of the two parents. This objective was substantially achieved, along with other desirable improvements, as evidenced by the following unique combination of characteristics that are outstanding in the new variety and that distinguish it from its parents, as well as from all other varieties of which I am aware:

1. Excellent petal substance;
2. Long, strong stems;
3. Good mildew resistance;
4. Novel flower color;
5. Glossy, dark green foliage; and
6. Heavily bearded sepals.

Asexual reproduction of this new variety by budding, as performed at Wasco, Calif., shows that the foregoing characteristics and all other features and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—MERko, U.S. Plant Pat. No. 3,724.

*Pollen parent.*—JACblem, U.S. Plant Pat. No. 4,847.

Classification:

*Botanical.*—Rosa hybrida.

*Commercial.*—Hybrid tea.

FLOWER

Observations made from specimens grown in a greenhouse environment at Somis, Calif., in January 1994 through January 1995.

Blooming habit: Continuous.

Bud:

*Size.*—1½ inches long when the petals start to unfurl.

*Form.*—The bud form is long, pointed ovoid.

*Color.*—When sepals first divide, bud color is Yellow Orange Group 21C. When half blown, the upper sides of the petals are Yellow Orange Group 21B; and the lower sides of the petals are Yellow Orange Group 21C.

*Sepals.*—Color: Green Group 138B. Surface texture: Covered in fine hairs. There are three heavily appendaged sepals. There are two sepals with extended tips that may or may not be appendaged, but do have hairy edges.

*Receptacle.*—Color: Green Group 143C. Shape: Funnel. Size: Large (5/16 inch by 5/16 inch). Surface: Smooth.

*Peduncle.*—Length: Long (4 to 4½ inches). Surface: Prickly. Color: Medium green. Strength: Stiff, erect.

Bloom:

*Size.*—Medium. Average open size is 4 to 4½ inches.

*Borne.*—Singly.

*Stems.*—Long, strong. Average length is about 24 to 28 inches.

*Form.*—When first open: High centered. Permanence: Retains its form to the end, outer petals curl back, quill fashion.

*Petalage.*—Number of petals under normal conditions: 30.

*Color.*—The upper side of each petal is Yellow Orange Group 21B. The reverse side of each petal is Yellow Orange Group 21C. The base of each petal has a distinctive, deep yellow (Yellow Group 12A) ¼ inch by ¼ inch, half moon at the point of attachment. The major color on the upper side is Yellow Orange Group 21B.

*Variegations.*—Occasional greenish streak on the mid rib of the guard petals.

*Discoloration.*—The general tonality at the end of the first day: No change. At the end of the third day, no change. By day 6, the color fades to Yellow Orange Group 21C; and, on day 7, to Yellow Orange Group 21D.

*Fragrance.*—Moderate.

Petals:

*Texture.*—Thick, leathery.

*Shape.*—Round to slightly deltoid.

*Form.*—Tips slightly recurved, edges slightly quilled.

*Arrangement.*—Imbricated, with few petaloids in the center.

*Persistence.*—Fall off cleanly.
*Lastingness.*—On the plant: 7 to 8 days. As a cut flower: 10 to 12 days.

Reproductive parts:
*Anthers.*—Size: Large. Quantity: Many. Color: Yellow. Arrangement: Regular around styles.
*Filaments.*—Color: Red.
*Pollen.*—Color: Gold yellow.
*Styles.*—Color: White.
*Stigmas.*—Color: Greenish white.

Form: Bush.

Growth: Very vigorous; upright; branching. Height at one year in a greenhouse will be 6 to 7 feet tall, and 3 to 4 feet wide. Plant produces 180 to 200 stems per square meter of greenhouse.

Foliage: Number of leaflets on normal mid-stem leaves: 5.
*Size.*—Large (6 to 6½ inches by 4 to 4½ inches).
*Quantity.*—Abundant.
*Color.*—New foliage: Upper and lower surface: Greyed Orange 176A. Old foliage: Upper surface: Green Group 139A. Lower surface: Green Group 138B.

Leaflets:
*Shape.*—Pointed oval.
*Texture.*—Upper side: leathery, glossy.
*Edge.*—Serrated.
*Serration.*—Single, small.
*Petiole rachis.*—Color: Green.
*Petiole underside.*—Smooth.
*Stipules.*—Long (¾ inch), and narrow; bearded.
*Disease resistance:* Resistant to mildew under normal greenhouse growing conditions at Somis, Calif.

Wood:
*New wood.*—Color: Reddish. Bark: Smooth.
*Old wood.*—Color: Green. Bark: Smooth.

Prickles:
*Quantity.*—On main canes from base: Ordinary. On laterals from main canes: Ordinary.
*Form.*—Medium (⅜ inch long); hooked slightly downward.
*Color when young.*—Green.

Small prickles:
*Quantity.*—On main stalks: Few. On laterals: Few.
*Color.*—Green.

I claim:

1. A new and distinct variety of rose plant of the hybrid tea class, substantially as herein shown and described, characterized particularly as to novelty by the unique combination of its novel flower color; its dark green, glossy, powdery mildew resistant foliage; its long, strong stems; its excellent petal substance, and its heavily appendaged sepals.

* * * * *

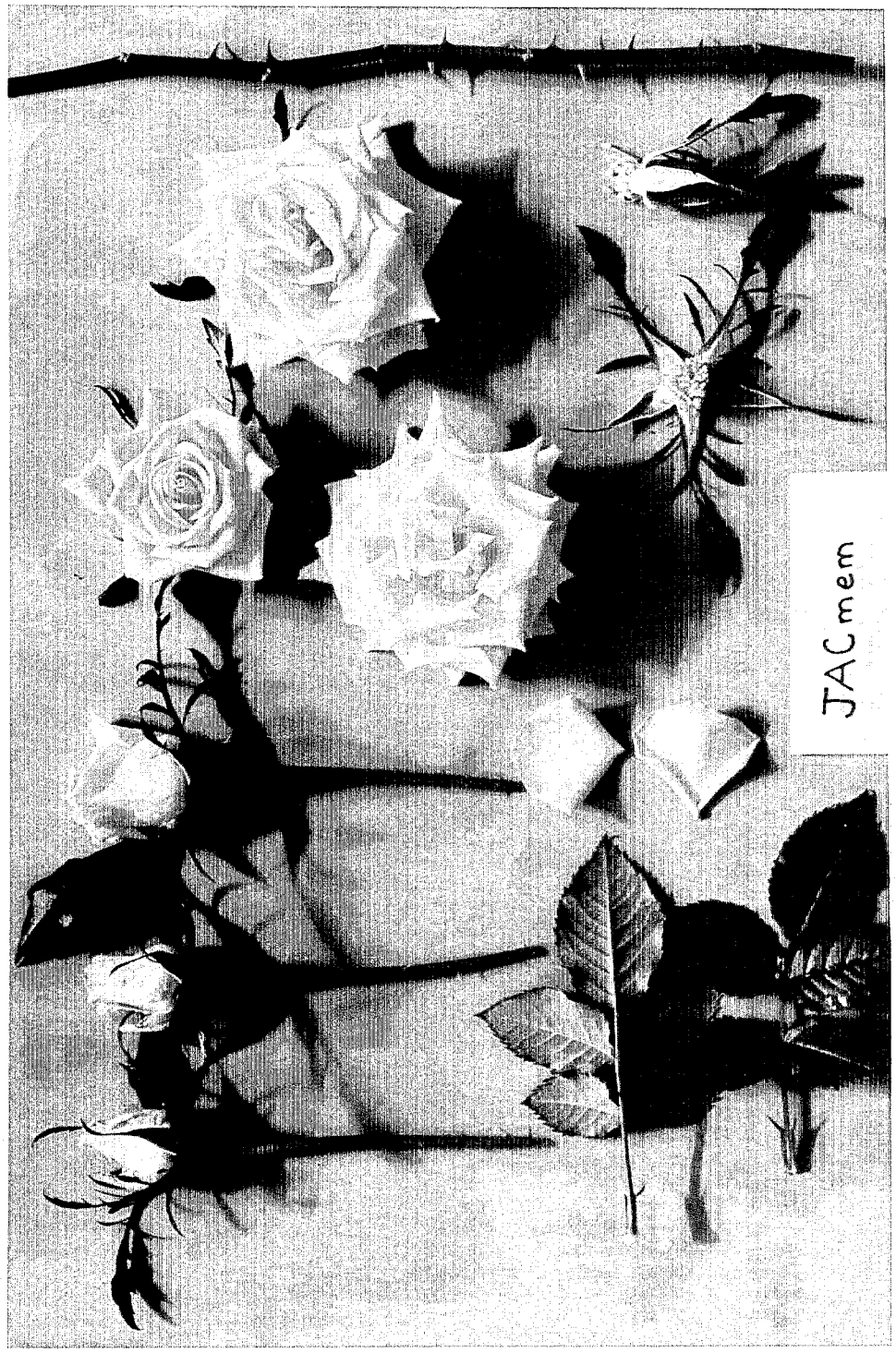
JACmem